United States Patent [19]
Williams et al.

[11] Patent Number: 6,025,408
[45] Date of Patent: Feb. 15, 2000

[54] LIQUID THIOXANTHONE PHOTOINITIATORS

[75] Inventors: Eric Lee Williams, Pascagoula, Miss.; Ruicheng Ran, Miamisburg, Ohio; Charles Uriah Pittman, Jr., Starkville, Miss.; Joseph Stanton Bowers, Jr.; August John Muller, both of Mobile, Ala.

[73] Assignee: First Chemical Corporation, Pascagoula, Miss.

[21] Appl. No.: 08/828,162

[22] Filed: Mar. 27, 1997

[51] Int. Cl.⁷ ............................ C08F 2/50; C07D 335/04; G03C 1/73
[52] U.S. Cl. ............................... 522/53; 522/16; 522/26; 522/53; 522/107; 522/182; 430/281.1; 546/110; 549/27
[58] Field of Search ................... 522/16, 26, 53, 522/107, 182; 546/110; 549/27; 430/281.1

[56] References Cited

U.S. PATENT DOCUMENTS

| | | |
|---|---|---|
| 3,857,769 | 12/1974 | McGinniss . |
| 3,876,519 | 4/1975 | McGinniss . |
| 4,299,772 | 11/1981 | Traxler . |
| 4,348,530 | 9/1982 | Kvita et al. . |
| 4,385,182 | 5/1983 | Fischer et al. . |
| 4,418,138 | 11/1983 | Curtis . |
| 4,437,959 | 3/1984 | Hayase et al. . |
| 4,450,279 | 5/1984 | Shirosaki et al. . |
| 4,459,416 | 7/1984 | Curtis et al. . |
| 4,505,794 | 3/1985 | Kvita et al. . |
| 4,506,083 | 3/1985 | Kvita et al. . |
| 4,590,145 | 5/1986 | Itoh et al. . |
| 4,594,400 | 6/1986 | Kvita et al. . |
| 4,602,097 | 7/1986 | Curtis ........................ 522/53 |
| 4,661,595 | 4/1987 | Avar ........................ 522/53 |
| 4,791,213 | 12/1988 | Gawne et al. . |
| 4,843,110 | 6/1989 | Kubota et al. . |
| 5,248,805 | 9/1993 | Boettcher et al. . |
| 5,310,909 | 5/1994 | Fischer et al. ................. 546/41 |
| 5,391,464 | 2/1995 | Afzali-Ardakani et al. . |
| 5,397,675 | 3/1995 | Arimatsu et al. . |
| 5,432,049 | 7/1995 | Fischer et al. ................. 522/53 |

FOREIGN PATENT DOCUMENTS

| | | | |
|---|---|---|---|
| 0281941 | 9/1988 | European Pat. Off. ............... 522/53 |
| 0 520 574 | 12/1992 | European Pat. Off. . |
| 195 02 025 | 7/1996 | Germany . |
| 2106101 | 4/1983 | United Kingdom ............... 522/53 |

OTHER PUBLICATIONS

Database WPI, Section CH, Week 9608 Derwent Publications Ltd., London, GB; Class A82, An 96–074911 XP002077852 & JP 07 330 816 A (Dainippon Ink & Chem Inc).

*Primary Examiner*—Susan W. Berman
*Attorney, Agent, or Firm*—Alston & Bird LLP

[57] ABSTRACT

Novel thioxanthone derivatives and mixtures thereof and methods of making and using the same are disclosed. The novel thioxanthone derivatives can be liquid at room temperature and display highly active photoinitiation and photopolymerization properties.

29 Claims, No Drawings

LIQUID THIOXANTHONE PHOTOINITIATORS

FIELD OF THE INVENTION

This invention relates to novel thioxanthone derivatives, and to methods for preparing and using the same.

BACKGROUND OF THE INVENTION

Ethylenically unsaturated compounds, and in particular acrylate derivatives, can be polymerized by irradiation with ultraviolet light of wavelength between 200 and 450 nanometers (nm) in the presence of a bimolecular photoinitiating system. Typically, the photoinitiating system includes (1) a thioxanthone derivative and optionally (2) a coinitiator or synergist, that is, a molecule which serves as a hydrogen atom donor. The coinitiators or synergists are typically alcohols, tertiary amines or ethers which have available hydrogens attached to a carbon adjacent to a heteroatom.

Examples of widely used commercially available thioxanthone derivatives which can be a component of a bimolecular photoinitiator system include 2-chlorothioxanthone (CTX) and a mixture of 2- and 4-isopropylthioxanthone (ITX). However, these and other commercially available thioxanthone photoinitiators are crystalline or powdered solids. Thus, they can be difficult to incorporate into photopolymerizable systems which are typically liquid.

Specifically, due to their solid nature and often poor solubility, incorporating these thioxanthone photoinitiators into a photopolymerization system requires either dissolving the compound in a monomer or milling the compound to achieve thorough dispersion. Dissolution into a monomer adds manufacturing steps, which can increase labor costs. Dissolution can also produce unstable solutions which can polymerize unexpectedly during extended stirring times and heating.

Milling powdered or crystalline photoinitiators into a photopolymerization system can also cause problems. For example, some initiators will stick to the steel rolls used in milling, which can make dispersion difficult. Stability can also be compromised if a relatively high concentration of initiator in the photopolymerization system begins to react from the heat generated by the milling process.

U.S. Pat. No. 5,248,805 teaches thioxanthone derivatives having a spacer group, such as a carbonate group, to connect the thioxanthone sensitizer to an ethylenically unsaturated group. According to this patent, the unsaturation allows the sensitizer to polymerize into a growing polymer backbone and eliminates problems associated with extractability, migration and volatility. The '805 patent fails to recognize, however, that thioxanthone carbonates could provide a route to liquid thioxanthone photoinitiators.

Further, the '805 patent teaches that chloroformates used to synthesize thioxanthone derivatives react readily with nucleophiles, including water. According to the '805 patent, it is essential to exclude moisture by using dried non-nucleophilic solvents, e.g. acetonitrile, dichloromethane, dichloroethane, tetrahydrofuran, toluene, xylene, chlorobenzene, ethyl acetate, chloroform, and the like, and if necessary to maintain an inert atmosphere, for example nitrogen, argon or carbon dioxide.

SUMMARY OF THE INVENTION

It is accordingly an object of the present invention to provide compounds which can be used as photoinitiators in photopolymerization processes, and which are liquid at room temperature. This is advantageous because liquid derivatives can dissolve readily in photopolymerization systems, thus overcoming the problems associated with solid photoinitiators as described above. These and other objects of the present invention will become apparent from the following general and detailed description of the invention.

The objects of the present invention are achieved based on the discovery of novel compounds useful in photopolymerization systems. The compounds, which are thioxanthone derivatives, are liquid at room temperature and display highly active photoinitiation and photopolymerization properties. The compounds of the invention have a structure according to Formula (I) below:

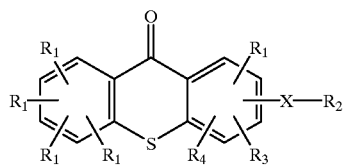

wherein:

each $R_1$ is independently selected from the group consisting of hydrogen; halogen; C1–C12 alkyl; C3–C6 cycloalkyl; and C1–C12 alkoxy;

$R_3$ and $R_4$ are each independently selected from the group consisting of hydrogen; halogen; C1–C18 alkyl; C3–C6 cycloalkyl; and C1–C18 alkoxy;

X is O or S; and $R_2$ is selected from the group consisting of $R_5$,

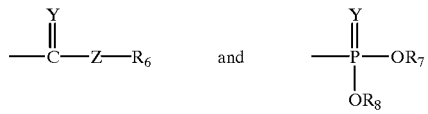

wherein:

each Y is independently selected from O or S;

Z is O or S;

$R_5$ and $R_6$ are each independently selected from the group consisting of C1–C18 alkyl; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl; and $R_7$ and $R_8$ are each independently selected from the group consisting of C1–C18 alkyl; C1–C12 alkoxy; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl.

The present invention also provides photopolymerizable compositions which include the compounds of Formula (I)

above as a component thereof, as well as methods for the manufacture of the compounds of Formula (I) and methods for the use of the compounds of Formula (I) in photopolymerization systems.

DETAILED DESCRIPTION OF THE INVENTION

The novel compounds of the invention include compounds according to Formula (I) below:

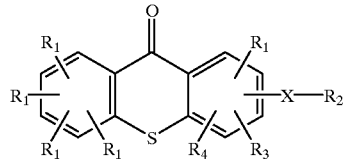

wherein:
  each $R_1$ is independently selected from the group consisting of hydrogen; halogen; C1–C12 alkyl; C3–C6 cycloalkyl; and C1–C12 alkoxy;
  $R_3$ and $R_4$ are each independently selected from the group consisting of hydrogen; halogen; C1–C18 alkyl; C3–C6 cycloalkyl; and C1–C18 alkoxy;
  X is O or S; and
  $R_2$ is selected from the group consisting of $R_5$,

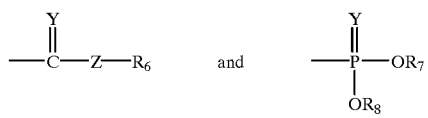

wherein:
  each Y is independently selected from O or S;
  Z is O or S;
  $R_5$ and $R_6$ are each independently selected from the group consisting of C1–C18 alkyl; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl; and
  $R_7$ and $R_8$ are each independently selected from the group consisting of C1–C18 alkyl; C1–C12 alkoxy; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl.

Preferred compounds of Formula I are those in which:
  $R_1$, $R_3$, and $R_4$ are each independently selected from the group consisting of H, C1–C4 alkyl, more preferably methyl or ethyl, and halogen, more preferably chloro or bromo;

X is O; and
$R_2$ is selected from the group consisting of $R_5$, a carbonate group

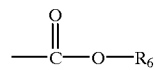

wherein Y and Z are each O; and a phosphate group

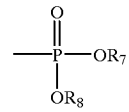

wherein Y is O;
  wherein $R_5$, $R_6$, $R_7$, and $R_8$ are each independently selected from C1–C8 straight chain or branched alkyl, more preferably isopropyl, 2-ethylhexyl, and 1-ethyl-2-methylpentyl; and
  wherein —X—$R_2$ is at the 2- or 4-position of the thioxanthone compound.

Exemplary compounds in accordance with Formula I include but are not limited to:

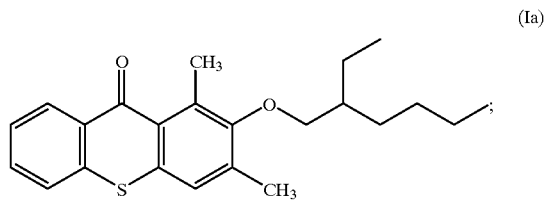

(Ia)

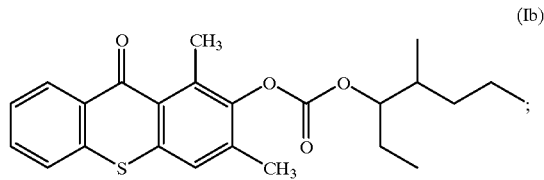

(Ib)

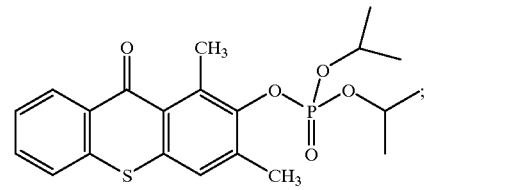

(Ic)

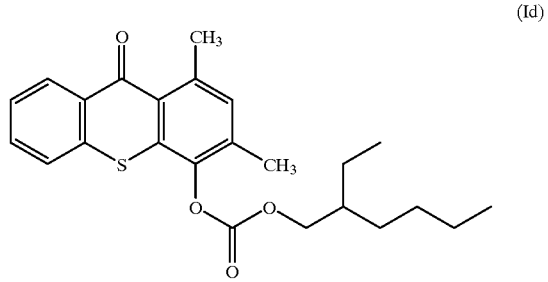

(Id)

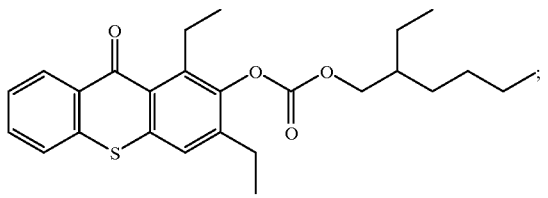
(Ie)

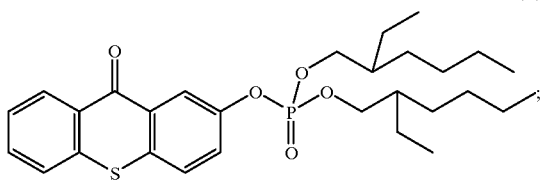
(If)

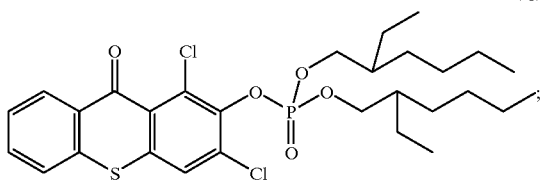
(Ig)

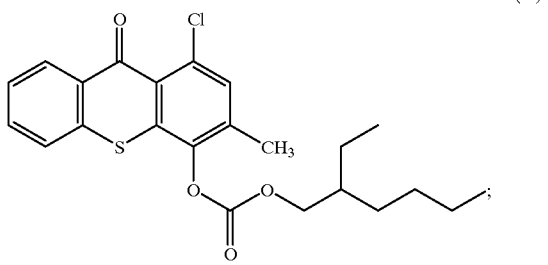
(Ih)

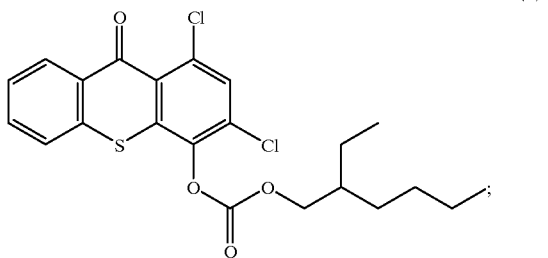
(Ii)

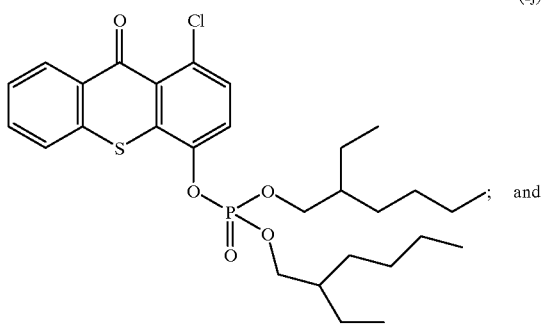
(Ij)

and

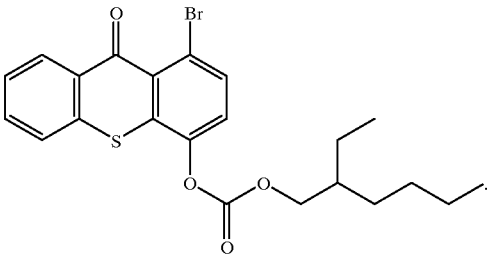
(Ik)

Generally, the carbonate compounds of Formula (I) are prepared by reacting haloformates, such as chloroformates, and alcohols in a biphasic medium consisting of a basic aqueous solution and an immiscible organic solvent. Advantageously, a phase transfer catalyst can be added to the biphasic to accelerate the desired reaction without causing an undesired loss of the reactive chloroformate. Other compounds of Formula (I), including phosphonates, ethers, and the like, can be prepared according to this same procedure except substituting haloformate with the appropriate reagent, such as phosphoryl halide, alkyl halide, and the like.

Suitable alcohols include those prepared according to the processes described in UK Patent Nos. 2,108,487 and 2,108,979, the entire disclosure of each of which is hereby incorporated by reference. For example, 2-hydroxythioxanthone can be prepared from thiosalicylic acid (TSA) or dithiosalicyclic acid (DTSA) and phenol as described in UK Patent Nos. 2,108,487 and 2,108,979. Other substituted hydroxythioxanthones can also be prepared from the aforementioned processes with slight modifications as will be appreciated by the skilled artisan.

The preparation of thioxanthone carbonates have also been described in U.S. Pat. No. 5,248,805, the entire disclosure of which is hereby incorporated by reference. Synthesis of other aryl carbonates have been reviewed in: a) Houben-Weyl, Methoden der Organische Chemie, Vol.8, pages 75, 101–107, Thieme-Verlag 1952; b) Kirk-Othmer, Encyclopedia of Industrial Chemistry, Vol.4, pages 758–771, John Wiley 1978; and c) Ulmann's Encyclopedia of Industrial Chemistry, Vol.A5, pages 197–202, Verlag Chemie 1986, the entire disclosure of each of which is also hereby incorporated by reference. In particular, preparations involving the reaction of chloroformates with alcohols are most applicable to this invention. These preparations are described in a) Houben-Weyl, Vol.8 (cited above); DE 1,080,546; and J. Org. Chem., 26, 5119 (1961), the entire disclosure of each of which is hereby incorporated by reference. Good yields of carbonates are generally obtained by reacting the chloroformates with alcohols in a molar ratio of about 1:1 in the absence or the presence of an aprotic solvent.

As noted above, U.S. Pat. No. 5,248,805 teaches that the chloroformates used in the reaction react readily with nucleophiles, including water. In the reaction, the '805 patent states that it is therefore essential to exclude moisture by using dried non-nucleophilic solvents, e.g. acetonitrile, dichloromethane, dichloroethane, tetrahydrofuran, toluene, xylene, chlorobenzene, ethyl acetate, chloroform, and the like, and if necessary to maintain an inert atmosphere, for example nitrogen, argon or carbon dioxide.

The inventors, however, have found that it is unnecessary to exclude moisture in the reaction of chloroformates and alcohols when the reaction is conducted in a biphasic medium consisting of a basic aqueous solution and an immiscible organic solvent. Furthermore, the addition of a phase transfer catalyst to the biphasic mixtures greatly accelerates the desired reaction without causing an undesired loss of the reactive chloroformate.

The ability to prepare the thioxanthone carbonate in the presence of water makes drying of the intermediate hydroxythioxanthone and the reaction solvents unnecessary. Consequently, because the hydroxythioxanthone is isolated from an aqueous medium and drying is unnecessary, the process can be carried out in one pot which results in considerable cost savings.

In another embodiment of the invention, photopolymerizable compositions are provided which include a compound of Formula (I) above as a photoinitiator. As used herein, and as will be appreciated by the skilled artisan, the term photopolymerizable composition refers to compositions which harden or cure upon exposure to radiation.

Generally the compositions of the invention include ethylenically unsaturated compounds, including monomers, oligomers, polymers, prepolymers, resinous materials, optionally dispersed or dissolved in a suitable solvent that is copolymerizable therewith, and mixtures thereof, which are photopolymerizable when exposed to a source of ultraviolet ("UV") radiation. As will be appreciated by the skilled artisan, the photopolymerizable compounds can be monofunctional, or can include two or more terminal polymerizable ethylenically unsaturated groupings per molecule.

Exemplary photopolymerizable compounds or precursors include, but are not limited to, reactive vinyl monomers, including acrylic monomers, such as acrylic and methacrylic acids, and their amides, esters, salts and corresponding nitrites. Suitable vinyl monomers include, but are not limited to, methyl acrylate, ethyl acrylate, n- or tert-butylacrylate, isooctyl acrylate, methyl methacrylate, ethylmethacrylate, 2-ethylhexyl methacrylate, butylacrylate, isobutyl methacrylate, the corresponding hydroxy acrylates, i.e., hydroxy ethylacrylate, hydroxy propylacrylate, hydroxy ethylhexyl methacrylate, glycol acrylates, i.e., ethylene glycol dimethacrylate, hexamethylene glycol dimethacrylate, the allyl acrylates, i.e., allyl methacrylate, diallyl methacrylate, the epoxy acrylates, i.e., glycidyl methacrylate, and the aminoplast acrylates, i.e., melamine acrylate. Others such as vinyl acetate, vinyl and vinylidene halides and amides, i.e., methacrylamide, acrylamide, diacetone acrylamide, butadiene, styrene, vinyl toluene, and the like are also included. Prepolymers include acrylated epoxides, polyesters and polyurethanes, and are typically combined with a suitable monomer for viscosity control. The photopolymerizable compounds may be polymerized to form homopolymers or copolymerized with various other monomers.

The photopolymerizable compound can be present in the compositions of the invention in amounts between about 99.8 and about 90 percent by weight of the composition, preferably between about 99.5 and about 95 percent by weight.

In this aspect of the invention, the compounds of Formula (I) act as photopolymerization initiators. The compounds of Formula (I) are added to the photopolymerizable compound in an amount sufficient to initiate polymerization thereof upon exposure to radiation. Preferably the compounds of Formula (I) are present in the photopolymerizable composition an amount between about 0.2 and 10 parts by weight of the composition, and more preferably between about 0.5 and about 5 parts by weight, depending on the specific application.

The use of the compounds of Formula (I) can provide improved cure rates as compared to conventional photoinitiators such as isopropylthioxanthone ("ITX"), particularly for clear compositions (i.e., in the absence of a colorant, i.e., a dye or pigment). However, one advantage of the photopolymerizable compositions of the invention which include a compound of Formula (I) as a photoinitiator is that many useful pigments can be incorporated into the composition. In particular, the use of the compounds of Formula (I) can provide cure rates for pigmented compositions which are at least comparable to those exhibited by ITX. This is advantageous because the addition of many pigments to photopolymerizable compositions can result in increased difficulties in curing those compositions by ultraviolet radiation.

Thus, the compositions of the invention can also include any of the various pigments, organic and inorganic, known in the art. Exemplary pigments include, but are not limited to, opacifying pigments such as zinc oxide, titania, e.g., anatase and rutile; basic lead sulfate, magnesium silicate, silica, clays, wollastonite, talcs, mica, chromates, iron pigments, wood fluor, microballons, hard polymer particles, glass fiber or flake. Pigments can be present in the compositions of the invention in conventional amounts, i.e., between about 1 and about 40 percent by weight.

It can also be advantageous to also include as a component of the compositions of the invention a coinitiator or synergist, that is, a molecule which serves as a hydrogen atom donor. Coinitiators or synergists are known in the art, and are typically alcohols, tertiary amines or ethers which have available hydrogens attached to a carbon adjacent to a heteroatom. Such coinitiators are typically present in an amount between about 0.2 and about 25 percent by weight. Suitable compounds include, but are not limited to, triethanolamine, methyl-diethanolamine, ethyldiethanolamine and esters of dimethylamino benzoic acid. Other known coinitiators or accelerators can also be used. These compounds behave as coinitiators or accelerators for the primary photoinitiators and can increase the efficiency and speed of the polymerization process.

In addition, the compositions of the present invention may contain polymerization inhibitors, fillers, ultraviolet absorbers and organic peroxides.

The compositions of the invention can be applied or deposited to a surface of a substrate using conventional techniques and apparatus. The composition can be applied as a substantially continuous film; alternatively, the composition can be applied in a discontinuous pattern. Usually the compositions of the invention are fluid at ordinary operating temperatures (between ambient and up to about 60° C.).

The thickness of the deposited composition can vary, depending upon the desired thickness of the resultant cured product. Advantageously, the composition is applied to the substrate surface in an amount sufficient to provide a cured coating having a thickness between about 1 micron and about 250 mils.

Typically, the substrate is coated with the uncured photopolymerizable composition and passed under an ultraviolet providing light beam by a conveyer moving at predetermined speeds. The substrate to be coated can be, for example, metal, mineral, glass, paper, plastic, fabric, ceramic, and the like.

The active energy beams used in accordance with the present invention may be ultraviolet light or may contain in their spectra both visible and ultraviolet light. The polymerization may be activated by irradiating the composition with ultraviolet light using any of the techniques known in the art for providing ultraviolet radiation, i.e., in the range of 240 nm and 420 nm ultraviolet radiation, or by irradiating the composition with radiation outside of the ultraviolet spectrum. The radiation may be natural or artificial, monochromatic or polychromatic, incoherent or coherent and should be sufficiently intense to activate the photoinitiators of the invention and thus the polymerization. Conventional radiation sources include fluorescent lamps, mercury, metal additive and arc lamps. Coherent light sources are the pulsed nitrogen, xenon, argon ion- and ionized neon lasers whose emissions fall within or overlap the ultraviolet or visible absorption bands of the compounds of the invention. In one embodiment of the invention, the composition including the compounds of the invention is exposed to ultraviolet radiation having a wavelength of about 240 to about 420 nm.

When polymerized by exposure to UV radiation, the compositions of the invention give a substantially tack-free product which is durable for ordinary handling. The compositions of the invention are useful in any of the types of applications known in the art for photopolymerizations, including as a binder for solids to yield a cured product in the nature of a paint, varnish, enamel, lacquer, stain or ink. The compositions are particularly useful in the production of photopolymerizable surface coatings in printing processes, such as lithographic printing, screen printing, and the like.

The present invention will be further illustrated by the following non-limiting examples.

Preparation of Hydroxythioxanthones

EXAMPLE 1

2,2'-Dithiosalicylic acid (46 grams, 0.15 mol) was placed in a 1-liter, round-bottom flask fitted with a mechanical stirrer, thermocouple, dropping funnel, nitrogen inlet, and an ice cooled bath. With cooling and while under nitrogen, 400 mL (7.5 mol) of 98% sulfuric acid was added. The slurry was stirred for 10 minutes, then 73 grams (0.60 mol) of fused 2,6-dimethylphenol was added via the dropping funnel over a 15 minute period while the temperature of the reaction held at about 15° C. to about 19° C.

After all the phenol was added, the cooling bath was removed and the mixture was stirred at 22° C. for 18 hours. The dark red reaction mixture was quenched by addition over 15 minutes to 2 liters of well stirred water. The yellow suspension of product which formed was filtered, and the filter cake was rinsed with warm water followed by drying in a vacuum oven at 60° C. overnight. 1,3-Dimethyl-2-hydroxythioxanth-9-one (66 grams) was obtained having a melting point (MP) of 181–184° C.

EXAMPLE 2

The procedure of Example 1 was followed, except for substituting 2,4-dimethyphenol for 2,6-dimethylphenol to obtain 1,3-dimethyl-4-hydroxythioxanth-9-one.

EXAMPLE 3

The procedure of Example 1 was followed, except for substituting 2,6-diethylphenol to obtain 1,3-diethyl-2-hydroxythioxanth-9-one.

EXAMPLE 4

The procedure of Example 1 was followed, except for substituting phenol to obtain 2-hydroxythioxanth-9-one.

EXAMPLE 5

The procedure of Example 1 was followed, except for substituting 2,6-dichlorophenol to obtain 1,3-dichloro-2-hydroxythioxanth-9-one.

EXAMPLE 6

The procedure of Example 1 was followed, except for substituting 2,4-dichlorophenol to obtain 1,3-dichloro-4-hydroxythioxanth-9-one.

EXAMPLE 7

The procedure of Example 1 was followed, except for substituting 4-chloro-2-methylphenol to obtain 1-chloro-3-methyl-4-hydroxythioxanth-9-one.

EXAMPLE 8

The procedure of Example 1 was followed, except for substituting 4-chlorophenol to obtain 1-chloro-4-hydroxythioxanth-9-one.

EXAMPLE 9

The procedure of Example 1 was followed, except for substituting 4-bromophenol to obtain 1-bromo-4-hydroxythioxanth-9-one.

Preparation of Thioxanthone Carbonates

EXAMPLE 10

In order, 5.5 grams (0.02 mol) of 1-chloro-3-methyl-4-hydroxythioxanth-9-one, 40 mL of toluene, 20 mL of 10% sodium hydroxide solution, 50 mg of tetra n-butylammonium bromide, and 3.9 mL (0.02 mol) of 2-ethylhexyl chloroformate were combined in a 250 mL flask equipped with a mechanical stirrer. The mixture was well stirred until the solid hydroxythioxanthone salts disappeared (usually about two hours).

Upon completion of the reaction, the phases were separated, and the organic phase was washed with water, dried over anhydrous sodium sulfate, and concentrated to give a dark amber oil. The oil was purified by silica gel chromatography (elution with ethyl acetate; hexanes=1:15) to give 4.8 grams of product 1-chloro-3-methyl-4-(2-ethylhexylcarbonyldioxy)thioxanth-9-one (structure Ih) as an oil.

EXAMPLE 11

The procedure of Example 10 was followed, except for substituting 1,3-dimethyl-2-hydroxthioxanth-9-one for the hydroxythioxanthone and 1-ethyl-2-methylpentyl chloroformate for the 2-ethylhexyl chloroformate to obtain 1,3-dimethyl-2-(1-ethyl-2-methylpentylcarbonyldioxy) thioxanth-9-one (structure Ib).

EXAMPLE 12

The procedure of Example 10 was followed, except for reacting 1,3-diethyl-2-hydroxythioxanth-9-one with 2-ethylhexyl chloroformate to obtain 1,3-diethyl-2-(2-ethylhexylcarbonyldioxy)thioxanth-9-one (structure Ie).

EXAMPLE 13

The procedure of Example 10 was followed, except for reacting 1,3-dimethyl-4-hydroxythioxanth-9-one with 2-ethylhexyl chloroformate to obtain 1,3-dimethyl-4-(2-ethylhexylcarbonyldioxy)thioxanth-9-one (structure Id).

EXAMPLE 14

The procedure of Example 10 was followed, except for reacting 1,3-dichloro-4-hydroxythioxanth-9-one with 2-ethylhexyl chloroformate to obtain 1,3-dichloro-4-(2-ethylhexylcarbonyldioxy)thioxanth-9-one (structure Ii).

EXAMPLE 15

The procedure of Example 10 was followed, except for reacting 1-bromo-4-hydroxythioxanth-9-one with 2-ethylhexyl chloroformate to obtain 1-bromo-4-(2-ethylhexylcarbonyldioxy)thioxanth-9-one (structure Ik).

Preparation of Thioxanthone Phosphate Esters

EXAMPLE 16

In order, 5.2 grams (0.02 mol) of 1-chloro-4-hydroxythioxanth-9-one, 50 mL of methylene chloride, 5.2 mL of 500 sodium hydroxide solution, 100 mg of tetra n-butylammonium bromide, and 8.2 grams (0.024 mol) of bis(2-ethylhexyl)phosphoryl chloride were combined in a 250 mL flask equipped with a mechanical stirrer. The mixture was well stirred for 3 hours.

The heterogeneous reaction mixture was filtered through a celite filter, and the filter cake was rinsed with methylene chloride. The filtrate was washed with water and dried over anhydrous sodium sulfate. Concentration gave an amber oil which was purified by silica gel chromatography (elution with ethyl acetate: hexanes=1:10) to give 2.98 grams of 1-Chloro-4-hydroxythioxanth-9-one, bis(2-ethylhexyl) phosphate ester product (structure Ij) as an oil.

EXAMPLE 17

The general procedure of Example 16 was followed except substituting 2-hydroxythioxanth-9-one for the hydroxythioxanthone to obtain 2-hydroxythioxanth-9-one, bis(2-ethylhexyl)phosphate ester (structure If).

EXAMPLE 18

The procedure of Example 16 was followed, except for substituting 1,3-dichloro-2-hydroxythioxanth-9-one for the hydroxythioxanthone to obtain 1,3-dichloro-2-hydroxythioxanth-9-one, bis(2-ethylhexyl)phosphate ester (structure Ig).

EXAMPLE 19

The procedure of Example 16 was followed, except for substituting 1,3-dimethyl-2-hydroxythioxanth-9-one and bis (isopropyl)phosphoryl chloride, to obtain 1,3-dimethyl-2-hydroxythioxanth-9-one, bis(isopropyl)phosphate ester (structure Ij).

Preparation of Thioxanthone Ethers

EXAMPLE 20

5.1 grams (0.02 mol) of 1,3-dimethyl-4-hydroxythioxanth-9-one, 30 mL of toluene, 2.4 grams of sodium hydroxide, 3.6 mL of water, 30 mg of tetra n-butylammonium bromide, and 5.3 mL (3.03 mol) of 2 ethylhexyl bromide were combined in a 100 mL flask equipped with a mechanical stirrer. The mixture was well stirred and refluxed for 18 hours.

After the mixture cooled to room temperature, it was diluted with 30 mL of toluene and 30 mL of water. The two phases were separated, and the organic phase was washed with brine followed by drying over anhydrous sodium sulfate. The toluene solution of product was passed through a short plug of silica gel on a Buchner filter to remove polar impurities. The toluene solution was concentrated to give 6.06 grams of 1,3-dimethyl-2-(2-ethylhexyloxy)thioxanth-9-one product (structure Ia) as an oil.

Use of Liquid Thioxanthone Compounds as Photoinitiators

EXAMPLE 21

Compounds of formula (I) were tested in clear unpigmented and in blue and white pigmented photopolymerizable systems. All percentages in this example are by weight.

The clear formulation consisted of 57% UCB Radcure EB 80 (a polyester polyol derivative), 29% tripropylene glycol diacrylate, and 14% UCB Radcure OTA 480 (glyceryl propoxy triacrylate.) Photopolymerizable systems consisted of 92% clear formulation, 4% photoinitiator, and 4% methyl diethanolamine. Films were drawn to a thickness of 50 microns on paper and cured with a Fusion UV Systems D bulb with 400 watts/inch power.

The blue formulation consisted of 54% UCB Radcure EB 80 (a polyester polyol derivative), 27% tripropylene glycol diacrylate, 13% UCB Radcure OTA 480 (glyceryl propoxy triacrylate), and 6% beta phthalocyanine blue. Photopolymerizable systems consisted of 92% blue formulation, 4% photoinitiator, and 4% methyl diethanolamine. Films were drawn to a thickness of 12 microns on paper and cured with a Fusion UV Systems D bulb with 600 watts/inch power.

The white formulation consisted of 33% UCB Radcure EB 80 (a polyester polyol derivative), 17% tripropylene glycol diacrylate, 8% UCB Radcure OTA 480 (glyceryl propoxy triacrylate), and 42% titanium dioxide. Photopolymerizable systems consisted of 92% white formulation, 4% photoinitiator, and 4% methyl diethanolamine. Films were drawn to a thickness of 12 microns on paper and cured with a Fusion UV Systems D bulb with 600 watts/inch power.

Each photopolymerizable system was tested to determine the maximum belt speed at which the cured polymer passed the thumb-twist test. Comparatively, the photoinitiators iso-propylthioxanthone (ITX) and 1-chloro-4-propoxythioxanthone (CPTX) were also tested. Table 1 below presents the maximum belt speeds at which the ITX photopolymerizable systems cured sufficiently. For all other photoinitiators Table 1 presents the ratio of the belt speed of the compound tested to the belt speed obtained with ITX. For example, ITX sufficiently cured the clear formulation at a belt speed of 180 feet per minute, and photoinitiator Ic cured the clear formulation at a belt speed of 180 feet per minute, and photoinitiator Ic cured the clear formulation at 2 times the speed of ITX, or a belt speed of 360 feet per minute. Similarly, ITX sufficiently cured the white formulation at a belt speed of 55 feet per minute, and photoinitiator Ig cured the white formulation at 1.7 times the speed of ITX, or a belt speed of 93 feet per minute.

TABLE 1

| Initiator | White | Blue | Clear |
|---|---|---|---|
| Ia | 1.1 | 1 | 1.8 |
| Ic |  | 1 | 2 |
| Id | 0.5 | 0.4 | 1.5 |
| Ie | 0.5 | 0.2 | 0.8 |
| If | 1 | 1 | 1.6 |
| Ig | 1.7 | 1.2 | 2.9 |
| Ih | 0.5 | 0.6 | 2 |
| Ii | 0.5 | 0.6 | 1.7 |
| Ij | 1 | 0.9 | 2.3 |

TABLE 1-continued

| Initiator | White | Blue | Clear |
|---|---|---|---|
| CPTX | 1.5 | 1.4 | 2.1 |
| ITX (Typical Cure Speeds; ft./min.) | 55 | 140 | 180 |

The foregoing examples are illustrative of the present invention and are not to be construed as limiting thereof. The invention is defined by the following claims, with equivalents of the claims to be included therein.

That which is claimed is:

1. A compound which is liquid at room temperature having the Formula (I)

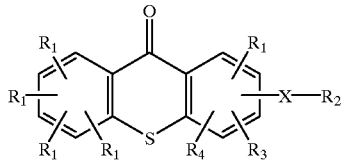

(I)

wherein:
each $R_1$ is independently selected from the group consisting of hydrogen; halogen; C1–C12 alkyl; C3–C6 cycloalkyl; and C1–C12 alkoxy;
$R_3$ and $R_4$ are each independently selected from the group consisting of hydrogen; halogen; C1–C18 alkyl; C3–C6 cycloalkyl; and C1–C18 alkoxy;
X is O or S; and
$R_2$ is selected from the group consisting of $R_5$,

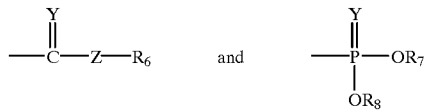

wherein:
each Y is independently selected from O or S;
Z is O or S;
$R_5$ and $R_6$ are each independently selected from the group consisting of C1–C18 alkyl; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl; and
$R_7$ and $R_8$ are each independently selected from the group consisting of C1–C18 alkyl; C1–C12 alkoxy; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl.

2. The compound of claim 1 wherein:
$R_1$, $R_3$, and $R_4$ are each independently selected from the group consisting of H, C1–C4 alkyl, and halogen;
X is O; and
$R_2$ is selected from the group consisting of $R_5$, a carbonate group

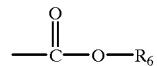

and a phosphate group

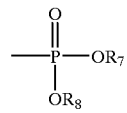

wherein $R_5$, $R_6$, $R_7$, and $R_8$ are each independently selected from C1–C8 straight chain or branched alkyl.

3. The compound of claim 2 wherein:
$R_1$, $R_3$, and $R_4$ are each independently selected from the group consisting of H, methyl, ethyl, chloro and bromo;
$R_5$, $R_6$, $R_7$, and $R_8$ are each independently selected from the group consisting of isopropyl, 2-ethylhexyl, and 1-ethyl-2-methylpentyl; and
—X—$R_2$ is at the 2- or 4- position of the thioxanthone compound.

4. The compound of claim 1 wherein:
$R_1$, $R_3$ and $R_4$ are each independently selected from C1–C4 alkyl or H;
X is O; and
$R_2$ is C1–C8 straight chain or branched alkyl.

5. The compound of claim 4 wherein:
$R_1$ and $R_3$ are each methyl located at the 1- and 3-position of the thioxanthone ring, respectively;
$R_4$ is H at the 4-position of the thioxanthone ring;
X is O at the 2-position of the thioxanthone ring; and
$R_2$ is 2-ethylhexyl.

6. The compound of claim 1, wherein:
$R_1$, $R_3$ and $R_4$ are each independently selected from the group consisting of C1–C4 alkyl, halogen and H;
X is O; and
$R_2$ is a carbonate

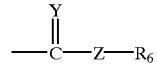

wherein each of Y and Z is O, and $R_6$ is C1–C8 straight chain or branched alkyl.

7. The compound of claim 6, wherein:
$R_1$ and $R_3$ are each independently selected from the group consisting of H, methyl, ethyl, chlorine, and bromine located at the 1- and 3-position of the thioxanthone ring, respectively;
$R_4$ is H at either the 2- or 4-position of the thioxanthone ring;
X is O at the 4-position of the thioxanthone ring when $R_4$ is at the 2-position of the thioxanthone ring, or X is O at the 2-position of the thioxanthone ring when $R_4$ is at the 4-position of the thioxanthone ring; and $R_6$ is 1-ethyl-2-methylpentyl or 2-ethylhexyl.

8. The compound of claim 1, wherein:
$R_1$, $R_3$ and $R_4$ are each independently selected from the group consisting of C1–C4 alkyl, halogen and H;
X is O; and
$R_2$ is a phosphate

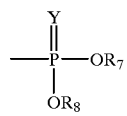

wherein Y is O; and wherein $R_7$ and $R_8$ are each independently selected from C1–C8 straight chain or branched alkyl.

9. The compound of claim 8, wherein:
$R_1$ and $R_3$ are each independently selected from the group consisting of H, methyl, ethyl, chlorine, and bromine located at the 1- and 3-position of the thioxanthone ring, respectively;
$R_4$ is H at either the 2- or 4-position of the thioxanthone ring;
X is O at the 4-position of the thioxanthone ring when $R_4$ is at the 2-position of the thioxanthone ring, or X is O at the 2-position of the thioxanthone ring when $R_4$ is at the 4-position of the thioxanthone ring; and
$R_7$ and $R_8$ are each isopropyl or 2-ethylhexyl.

10. A compound which is liquid at room temperature having the Formula (I)

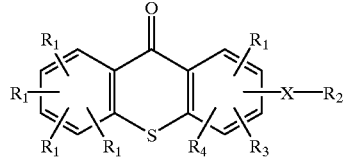

(I)

wherein:
each $R_1$ is independently selected from the group consisting of hydrogen; halogen; C1–C12 alkyl; C3–C6 cycloalkyl; and C1–C12 alkoxy;
$R_3$ and $R_4$ are each independently selected from the group consisting of hydrogen; halogen; C1–C18 alkyl; C3–C6 cycloalkyl; and C1–C18 alkoxy;
X is O; and
$R_2$ is selected from the group consisting of $R_5$,

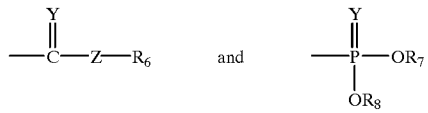

wherein:
each Y is O;
Z is O; and
$R_5$, $R_6$, $R_7$, and $R_8$ are each independently selected from C1–C18 branched alkyl.

11. The compound of claim 10 wherein:
$R_1$, $R_3$, and $R_4$ are each independently selected from the group consisting of H, methyl, ethyl, chloro and bromo;

$R_5$, $R_6$, $R_7$, and $R_8$ are each independently selected from the group consisting of isopropyl, 2-ethylhexyl, and 1-ethyl-2-methylpentyl; and —X—$R_2$ is at the 2- or 4- position of the thioxanthone compound.

12. A compound which is liquid at room temperature selected from the group consisting of:

(Ia)

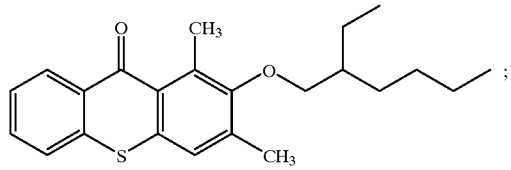

(Ib)

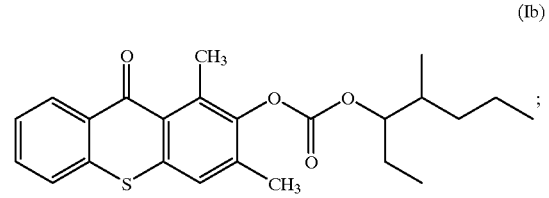

(Ic)

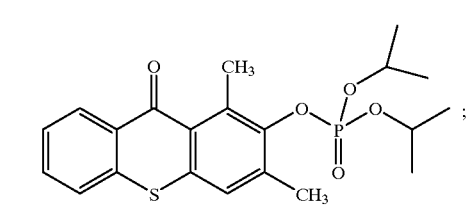

(Id)

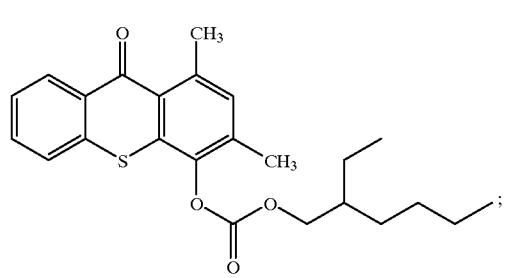

(Ie)

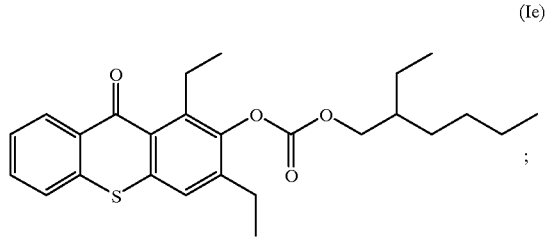

(If)

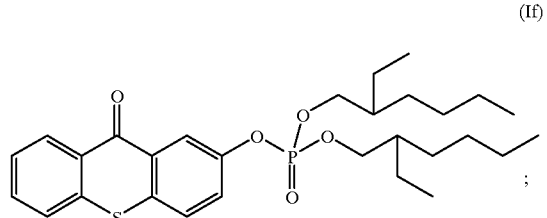

(Ig) 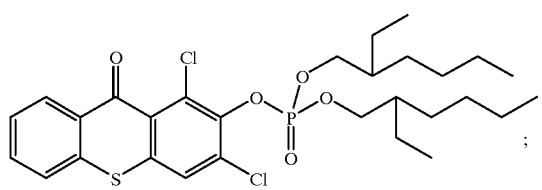

(Ih) 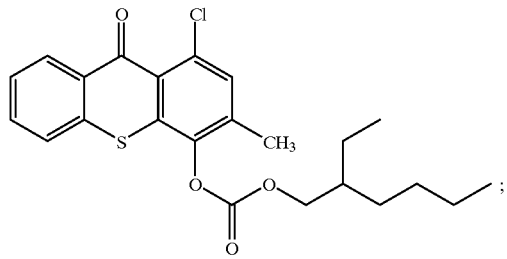

(Ii) 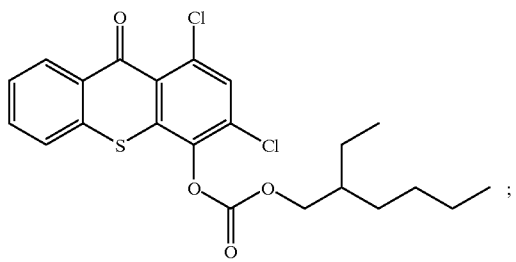

(Ij) 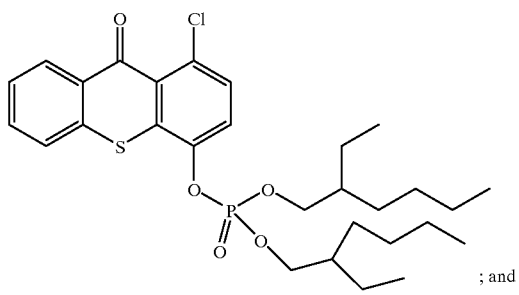

; and (Ik) 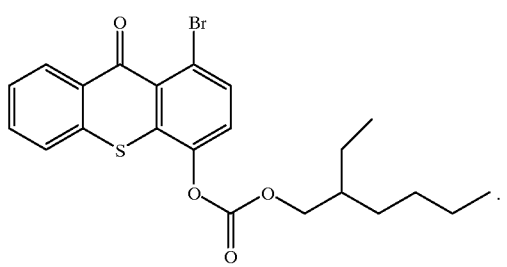

.

13. A compound having the Formula (I)

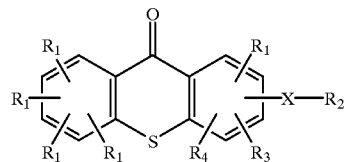

(I)

wherein:

$R_1$, $R_3$ and $R_4$ are each independently selected from the group consisting of C1–C4 alkyl, halogen, and hydrogen;

X is O; and $R_2$ is

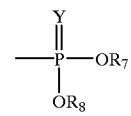

wherein Y is O and $R_7$ and $R_8$ are each independently selected from the group consisting of C1–C8 straight chain or branched alkyl.

14. The compound of claim 13, wherein:

$R_1$ and $R_3$ are each independently selected from the group consisting of H, methyl, ethyl, chlorine, and bromine located at the 1- and 3-position of the thioxanthone ring, respectively;

$R_4$ is H at either the 2- or 4-position of the thioxanthone ring;

X is O at the 4-position of the thioxanthone ring when $R_4$ is at the 2-position of the thioxanthone ring, or X is O at the 2-position of the thioxanthone ring when $R_4$ is at the 4-position of the thioxanthone ring; and $R_7$ and $R_8$ are each isopropyl or 2-ethylhexyl.

15. A compound which is liquid at room temperature having the Formula (I)

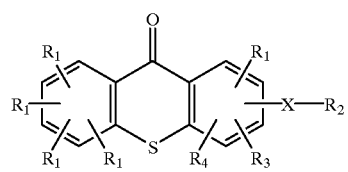

(I)

wherein:

each $R_1$ is independently selected from the group consisting of hydrogen; halogen; C1–C12 alkyl; C3–C6 cycloalkyl; and C1–C12 alkoxy;

$R_3$ and $R_4$ are each independently selected from the group consisting of hydrogen; halogen; C1–C18 alkyl; C3–C6 cycloalkyl; and C1–C18 alkoxy;

X is O or S; and $R_2$ is selected from the group consisting of 2-ethylhexyl,

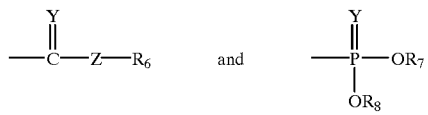 and 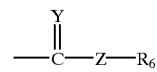

wherein:
each Y is independently selected from O or S;
Z is O or S;
$R_6$ is 1-ethyl-2-methylpentyl or 2-ethylhexyl; and
$R_7$ and $R_8$ are each independently selected from the group consisting of C1–C18 alkyl; C1–C12 alkoxy; C3–C6 cycloalkyl; C7–C24 alkylaryl; C2–C18 alkenyl; C1–C18 alkyl ether or polyether; phenyl, optionally substituted. with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl.

16. The compound of claim 15, wherein:

$R_1$, $R_3$, and $R_4$ are each independently selected from the group consisting of H, C1–C4 alkyl, and halogen;

X is O; and $R_2$ is selected from the group consisting of 2-ethylhexyl, a carbonate group

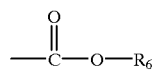

and a phosphate group

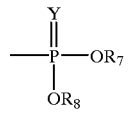

wherein $R_7$ and $R_8$ are each independently selected from C1–C8 branched alkyl.

17. The compound of claim 15 wherein:

$R_1$, $R_3$, and $R_4$ are each independently selected from the group consisting of H, methyl, ethyl, chloro and bromo; and —X—$R_2$ is at the 2- or 4- position of the thioxanthone compound.

18. The compound of claim 15 wherein:

$R_1$, $R_3$ and $R_4$ are each independently selected from C1–C4 alkyl or H;

X is O; and $R_2$ is of 2-ethylhexyl.

19. The compound of claim 15, wherein:

$R_1$, $R_3$ and $R_4$ are each independently selected from the group consisting of C1–C4 alkyl, halogen and H;

X is O; and $R_2$ is a carbonate

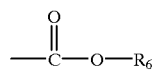

wherein each of Y and Z is O, and $R_6$ is 1-ethyl-2-methylpentyl or 2-ethylhexyl.

20. A photopolymerizable composition comprising a photopolymerizable compound comprising at least one ethylenically unsaturated double bond and a photoinitiator which is liquid at room temperature having the Formula (I)

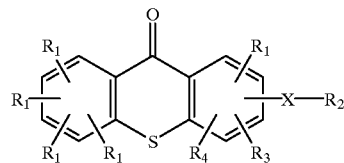

(I)

wherein:
each $R_1$ is independently selected from the group consisting of hydrogen; halogen; C1–C12 alkyl; C3–C6 cycloalkyl; and C1–C12 alkoxy;
$R_3$ and $R_4$ are each independently selected from the group consisting of hydrogen; halogen; C1–C18 alkyl; C3–C6 cycloalkyl; and C1–C18 alkoxy;
X is O or S; and
$R_2$ is selected from the group consisting of $R_5$,

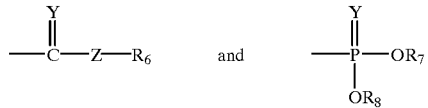

wherein:
each Y is independently selected from O or S;
Z is O or S;
$R_5$ and $R_6$ are each independently selected from the group consisting of C1–C18 alkyl; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl; and
$R_7$ and $R_8$ are each independently selected from the group consisting of C1–C18 alkyl; C1–C12 alkoxy; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl.

21. A photopolymerizable composition comprising a photopolymerizable compound comprising at least one ethylenically unsaturated double bond and a photoinitiator having the Formula (I)

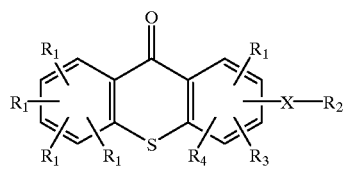

(I)

wherein:

R₁, R₃ and R₄ are each independently selected from the group consisting of C1–C4 alkyl, halogen, and hydrogen;

X is O; and

R₂ is

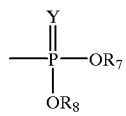

wherein Y is O and R₇ and R₈ are each independently selected from the group consisting of C1–C8 straight chain or branched alkyl.

22. The composition of claim 21, wherein:

R₁ and R₃ are each independently selected from the group consisting of H, methyl, ethyl, chlorine, and bromine located at the 1- and 3-position of the thioxanthone ring, respectively;

R₄ is H at either the 2- or 4-position of the thioxanthone ring;

X is O at the 4-position of the thioxanthone ring when R₄ is at the 2-position of the thioxanthone ring, or X is O at the 2-position of the thioxanthone ring when R₄ is at the 4-position of the thioxanthone ring; and R₇ and R₈ are each isopropyl or 2-ethylhexyl.

23. A photopolymerizable composition comprising a photopolymerizable compound comprising at least one ethylenically unsaturated double bond and a photoinitiator which is liquid at room temperature having the Formula (I)

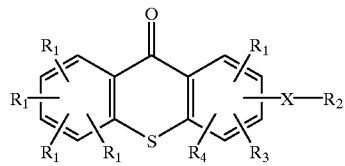

(I)

wherein:

each R₁ is independently selected from the group consisting of hydrogen; halogen; C1–C12 alkyl; C3–C6 cycloalkyl; and C1–C12 alkoxy;

R₃ and R₄ are each independently selected from the group consisting of hydrogen; halogen; C1–C18 alkyl; C3–C6 cycloalkyl; and C1–C18 alkoxy;

X is O or S; and

R₂ is selected from the group consisting of 2-ethylhexyl,

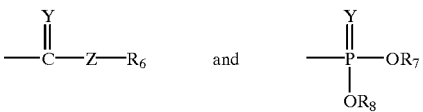

wherein:

each Y is independently selected from O or S;

Z is O or S;

R₆ is 1-ethyl-2-methylpentyl or 2-ethylhexyl; and

R₇ and R₈ are each independently selected from the group consisting of C1–C18 alkyl; C1–C12 alkoxy; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl.

24. A photopolymerizable composition comprising a photopolymerizable compound comprising at least one ethylenically unsaturated double bond and at least one photoinitiator which is liquid at room temperature selected from the group consisting of:

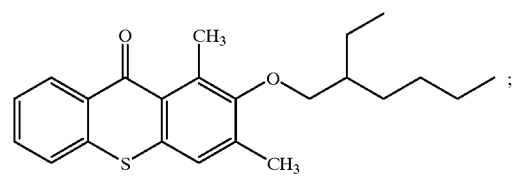

(Ia)

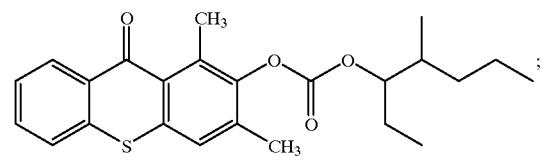

(Ib)

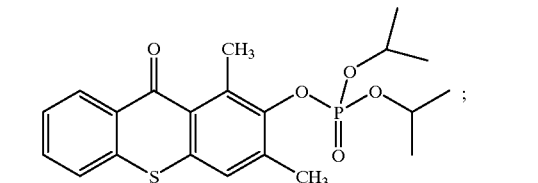

(Ic)

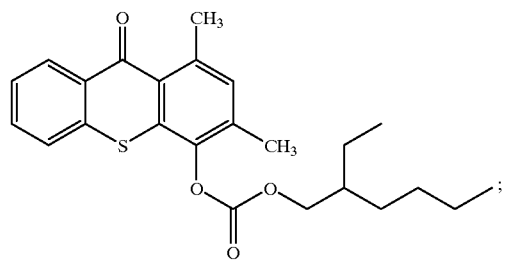

(Id)

-continued

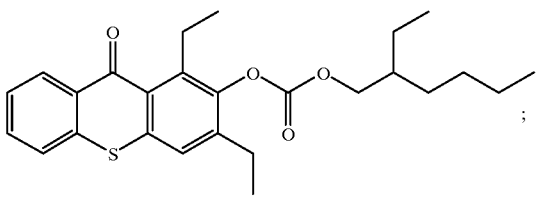
(Ie)

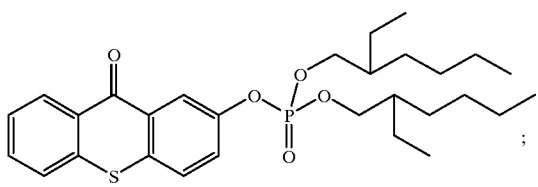
(If)

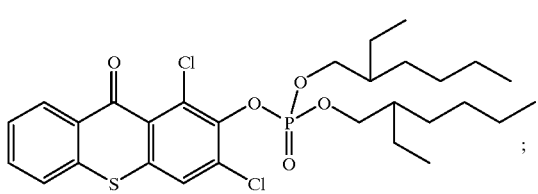
(Ig)

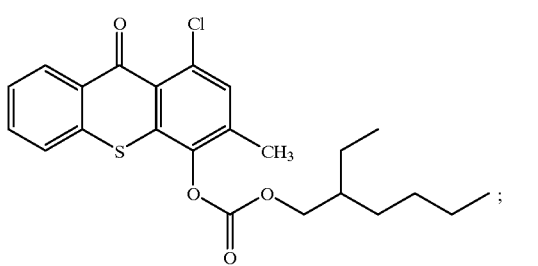
(Ih)

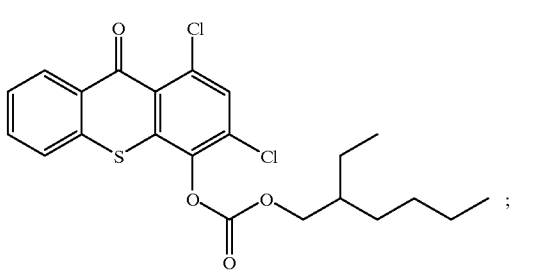
(Ii)

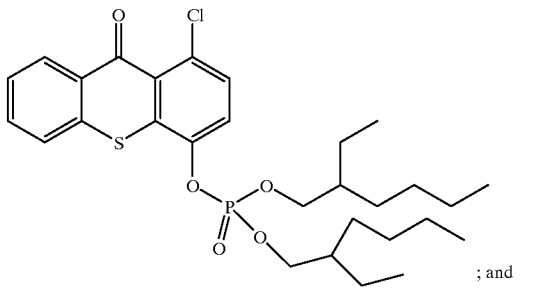
(Ij)

-continued

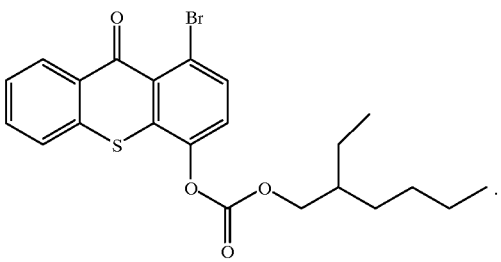
(Ik)

25. A method of polymerizing a polymerizable compound comprising at least one ethylenically unsaturated double bond, comprising exposing said compound to radiation in the presence of a compound which is liquid at room temperature having the Formula (I)

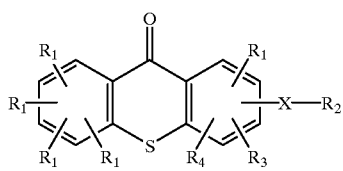
(I)

wherein:
each $R_1$ is independently selected from the group consisting of hydrogen; halogen; C1–C12 alkyl; C3–C6 cycloalkyl; and C1–C12 alkoxy;

$R_3$ and $R_4$ are each independently selected from the group consisting of hydrogen; halogen; C1–C18 alkyl; C3–C6 cycloalkyl; and C1–C18 alkoxy;

X is O or S;

$R_2$ is selected from the group consisting of $R_5$,

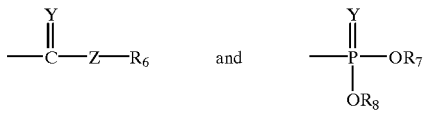

wherein:
each Y is independently selected from O or S;
Z is O or S;
$R_5$ and $R_6$ are each independently selected from the group consisting of C1–C18 alkyl; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl; and $R_7$ and $R_8$ are each independently selected from the group consisting of C1–C18 alkyl; C1–C12 alkoxy; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl.

26. A method of polymerizing a polymerizable compound comprising at least one ethylenically unsaturated double bond, comprising exposing said compound to radiation in the presence of a compound having the Formula (I)

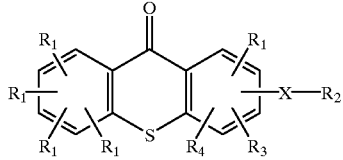
(I)

wherein:
R$_1$, R$_3$ and R$_4$ are each independently selected from the group consisting of C1–C4 alkyl, halogen, and hydrogen;
X is O; and
R$_2$ is

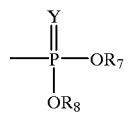

wherein Y is O and R$_7$ and R$_8$ are each independently selected from the group consisting of C1–C8 straight chain or branched alkyl.

27. The method of claim 26, wherein:
R$_1$ and R$_3$ are each independently selected from the group consisting of H, methyl, ethyl, chlorine, and bromine located at the 1- and 3-position of the thioxanthone ring, respectively;
R$_4$ is H at either the 2- or 4-position of the thioxanthone ring;
X is O at the 4-position of the thioxanthone ring when R$_4$ is at the 2-position of the thioxanthone ring, or X is O at the 2-position of the thioxanthone ring when R$_4$ is at the 4-position of the thioxanthone ring; and
R$_7$ and R$_8$ are each isopropyl or 2-ethylhexyl.

28. A method of polymerizing a polymerizable compound comprising at least one ethylenically unsaturated double bond, comprising exposing said compound to radiation in the presence of a compound which is liquid at room temperature having the Formula (I)

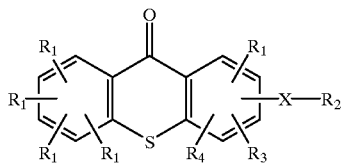
(I)

wherein:
each R$_1$ is independently selected from the group consisting of hydrogen; halogen; C1–C12 alkyl; C3–C6 cycloalkyl; and C1–C12 alkoxy;
R$_3$ and R$_4$ are each independently selected from the group consisting of hydrogen; halogen; C1–C18 alkyl; C3–C6 cycloalkyl; and C1–C18 alkoxy;

X is O or S;
R$_2$ is selected from the group consisting of 2-ethylhexyl,

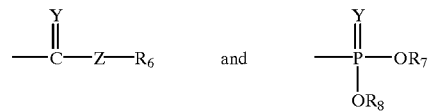

wherein:
each Y is independently selected from O or S;
Z is O or S;
R$_6$ is 1-ethyl-2-methylpentyl or 2-ethylhexyl; and
R$_7$ and R$_8$ are each independently selected from the group consisting of C1–C18 alkyl; C1–C12 alkoxy; C3–C6 cycloalkyl; C7–C24 alkylaryl; C2–C18 alkenyl; C1–C18 alkyl ether or polyether; phenyl, optionally substituted with halogen atoms, cyano groups, C1–C12 alkyl groups, C1–C12 alkoxy groups or nitro groups; and C1–C18 hydroxyalkyl, which hydroxy group may be alkylated by C1–C18 alkyl, C2–C18 alkenyl, C3–C6 cycloalkyl, C1–C10 alkanoyl, C1–C10 alkenoyl or acylated with C1–C10 alkanoyl or C1–C10 alkenoyl.

29. A method of polymerizing a polymerizable compound comprising at least one ethylenically unsaturated double bond, comprising exposing said compound to radiation in the presence of a compound which is liquid at room temperature selected from the group consisting of:

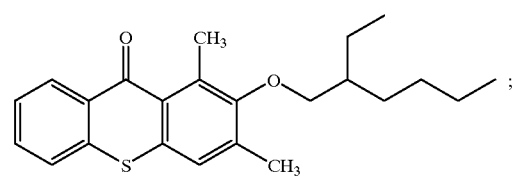
(Ia)

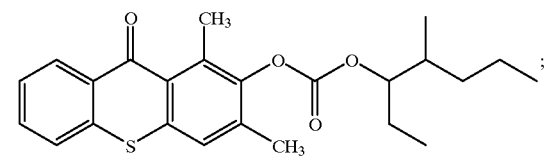
(Ib)

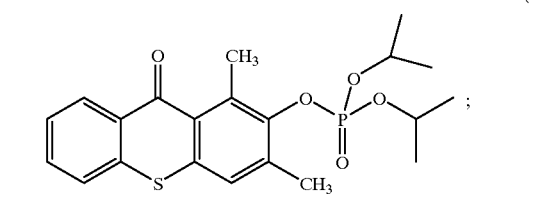
(Ic)

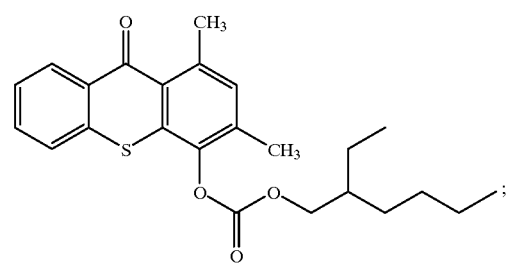
(Id)

(Ie)
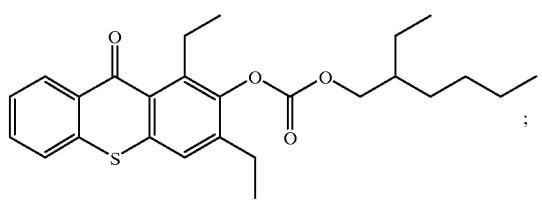
;
(If)
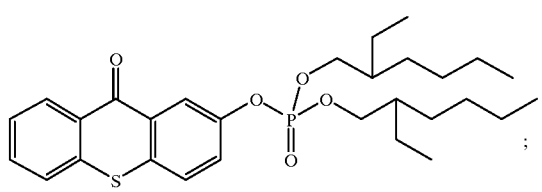
;
(Ig)
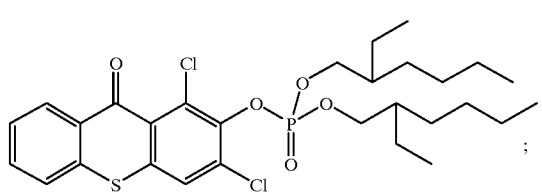
;
(Ih)
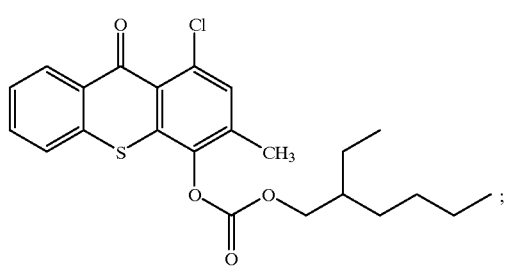
;
(Ii)
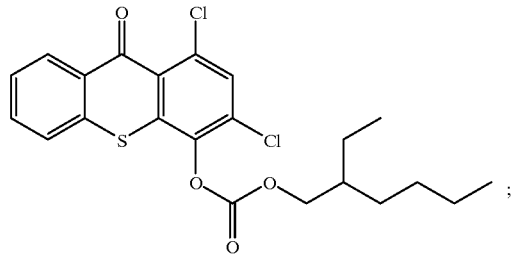
;
(Ij)
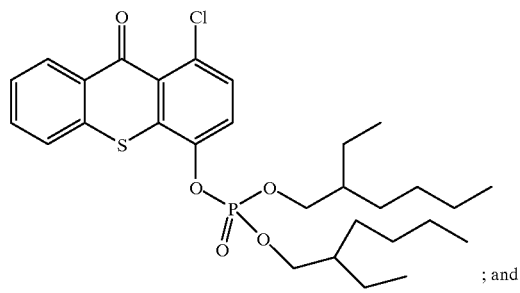
; and
(Ik)
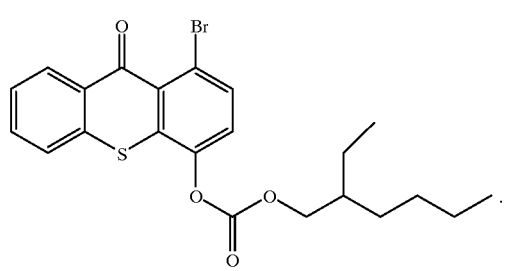
.
* * * * *

UNITED STATES PATENT AND TRADEMARK OFFICE
CERTIFICATE OF CORRECTION

PATENT NO. : 6,025,408

DATED : February 15, 2000

INVENTOR(S) : Williams et al.

It is certified that error appears in the above-identified patent and that said Letters Patent is hereby corrected as shown below:

Column 19, line 50, "claim 15" should read --claim 16--.

Signed and Sealed this

Thirtieth Day of January, 2001

Attest:

*Attesting Officer*

Q. TODD DICKINSON

*Director of Patents and Trademarks*